United States Patent
Han et al.

(10) Patent No.: US 12,178,796 B2
(45) Date of Patent: Dec. 31, 2024

(54) DRUG-LOADED NANOFIBER MEMBRANE, METHOD FOR PREPARING THE SAME, AND APPLICATION THEREOF

(71) Applicant: Shenzhen Guangyuan Biomaterial Co., Ltd., Shenzhen (CN)

(72) Inventors: Zhichao Han, Shenzhen (CN); Shanshan Xu, Shenzhen (CN); Jia'en Wu, Shenzhen (CN)

(73) Assignee: SHENZHEN GUANGYUAN BIOMATERIAL CO., LTD., Shenzhen (CN)

( * ) Notice: Subject to any disclaimer, the term of this patent is extended or adjusted under 35 U.S.C. 154(b) by 708 days.

(21) Appl. No.: 17/467,427

(22) Filed: Sep. 6, 2021

(65) Prior Publication Data

US 2021/0393568 A1    Dec. 23, 2021

Related U.S. Application Data

(63) Continuation-in-part of application No. PCT/CN2019/106837, filed on Sep. 20, 2019.

(30) Foreign Application Priority Data

Mar. 15, 2019   (CN) .......................... 201910197875.8

(51) Int. Cl.
| | | |
|---|---|---|
| *A61K 31/337* | (2006.01) | |
| *A61K 31/496* | (2006.01) | |
| *A61K 31/513* | (2006.01) | |
| *A61K 31/5383* | (2006.01) | |
| *A61K 31/545* | (2006.01) | |
| *A61K 31/7068* | (2006.01) | |
| *A61K 47/34* | (2017.01) | |
| *D01D 5/00* | (2006.01) | |
| *D04H 1/728* | (2012.01) | |

(52) U.S. Cl.
CPC .......... *A61K 31/337* (2013.01); *A61K 31/496* (2013.01); *A61K 31/513* (2013.01); *A61K 31/5383* (2013.01); *A61K 31/545* (2013.01); *A61K 31/7068* (2013.01); *A61K 47/34* (2013.01); *D01D 5/0069* (2013.01); *D04H 1/728* (2013.01); *D10B 2509/022* (2013.01)

(58) Field of Classification Search
CPC .. A61K 31/337; A61K 31/496; A61K 31/513; A61K 31/5383; A61K 31/545; A61K 31/7068; A61K 47/34; D01D 5/0069; D04H 1/728; D10B 2509/022
See application file for complete search history.

(56) References Cited

U.S. PATENT DOCUMENTS

| | | | |
|---|---|---|---|
| 8,974,814 B2 * | 3/2015 | Mack ................... | A61K 9/0051 424/443 |
| 2004/0151753 A1 * | 8/2004 | Chen .................... | A61K 9/0024 424/426 |
| 2009/0081457 A1 | 3/2009 | Nagarajan et al. | |
| 2011/0190886 A1 | 8/2011 | Li | |

FOREIGN PATENT DOCUMENTS

| | | |
|---|---|---|
| CN | 1481902 A | 3/2004 |
| CN | 101705529 A | 5/2010 |
| CN | 102397580 A | 4/2012 |
| CN | 102908665 A | 2/2013 |
| CN | 102921050 A | 2/2013 |
| CN | 103432631 A | 12/2013 |
| CN | 103966680 A | 8/2014 |
| CN | 105455923 A | 4/2016 |
| CN | 106676754 A | 5/2017 |
| CN | 106880585 A | 6/2017 |
| CN | 107059157 A | 8/2017 |
| CN | 107157960 A | 9/2017 |
| CN | 107537067 A | 1/2018 |
| CN | 107596448 A | 1/2018 |
| CN | 109414524 A | 3/2019 |
| CN | 109432062 A | 3/2019 |
| CN | 109898236 A | 6/2019 |
| CN | 109908108 A | 6/2019 |
| IN | 103757743 A | 4/2014 |

* cited by examiner

*Primary Examiner* — Michael P Cohen
(74) *Attorney, Agent, or Firm* — MATTHIAS SCHOLL P.C.; Matthias Scholl

(57) ABSTRACT

A drug-loaded nanofiber membrane includes a first fiber, a second fiber, and a drug. The drug is dispersed into the first fiber. The first fiber includes poly(lactic-co-glycolic acid) copolymer (PLGA copolymer), and the second fiber includes poly(p-dioxanone) (PDO).

9 Claims, 5 Drawing Sheets

DRUG-LOADED NANOFIBER MEMBRANE, METHOD FOR PREPARING THE SAME, AND APPLICATION THEREOF

CROSS-REFERENCE TO RELATED APPLICATIONS

This application is a continuation-in-part of International Patent Application No. PCT/CN2019/106837 with an international filing date of Sep. 20, 2019, designating the United States, now pending, and further claims foreign priority benefits to Chinese Patent Application No. 201910197875.8 filed Mar. 15, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of fiber membrane, and more particularly, to a drug-loaded nanofiber membrane, a method for preparing the same, and application thereof.

After surgery, various drugs are used orally, intravenously, or in combination to prevent infection, tumor spread and recurrence. However, the drug utilization rate through oral or intravenous administration is low and the oral or intravenous administration poses potential toxic effect. In addition, the local concentrations of the drugs often fail to reach the effective therapeutic level in the wound or lesion areas, leading to poor therapeutic effect.

In recent years, a biocompatible fiber membrane has been developed to carry drugs for targeted delivery. The drugs can be absorbed by wound tissues in situ to prevent local wound infection or tumor metastasis. Thereafter, the fiber membrane is adsorbed by human body.

Conventional drug-loaded fiber membranes are prepared by electrostatic spinning technology and can be divided into three categories: (1) fiber membrane loaded with drugs on the surface thereof; (2) polymer blended with drugs; and (3) a core-shell fiber membrane formed by coaxial electrospinning. For the above-mentioned drug-loaded fiber membranes, the drugs are released exponentially, not linearly, which is not conducive to the absorption of drugs.

SUMMARY

One objective of the disclosure is to provide a drug-loaded nanofiber membrane comprising a first fiber, a second fiber, and a drug; the drug is dispersed into the first fiber; the first fiber comprises poly(lactic-co-glycolic acid) copolymer (PLGA copolymer), and the second fiber comprises poly(p-dioxanone) (PDO).

In the disclosure, the poly(lactic-co-glycolic acid) copolymer and poly(p-dioxanone) form the first fiber and the second fiber, respectively, and the drug is dispersed into the first fiber; the first fiber has a relatively high swelling capacity, so that the first fiber swells in vivo and bonds together, thereby blocking the release of drug from the channels in the first fiber; the second fiber has a relatively low swelling capacity, and the fibers are difficult to bond together, thereby supporting the poly(lactic-co-glycolic acid) copolymer to form a part of channels for the release of the drug.

In a class of this embodiment, the PLGA copolymer is a mixture of a high-molecular weight PLGA copolymer and a low-molecular weight PLGA copolymer. The high-molecular weight refers to a viscosity-average molecular weight of 100,000 to 150,000 Da, such as 100,000 Da, 110,000 Da, 120,000 Da, 130,000 Da, 140,000 Da, or 150,000 Da. The low-molecular weight refers to a viscosity-average molecular weight of 40,000 to 80,000 Da, such as, 40,000 Da, 50,000 Da, 60,000 Da, 70,000 Da, or 80,000 Da.

A small amount of the high-molecular weight PLGA copolymer is added to the low-molecular weight PLGA copolymer to prepare the first fiber, thereby increasing the diameter of the first fiber and enabling an increase in swelling capacity to be achieved. Only a small amount of the high-molecular weight PLGA copolymer is added to increase the diameter of the first fiber. Too much high-molecular weight PLGA copolymer increases the viscosity of the polymer solution, which may affect the swelling capacity.

In a class of this embodiment, a mass ratio of the high-molecular weight PLGA copolymer to the low-molecular weight PLGA copolymer is between 25:75 and 3:97, such as 25:75, 20:80, 15:85, 12:88, 10:90, 8:92, 7:93, 6:96, 5:95, or 3:97.

The swelling of the first fiber is controlled mainly by the molecular weight and the mass ratio. The first fiber is swollen and completely bonded together when the high-molecular weight PLGA copolymer is 100000-150000 Da in the molecular weight, the low-molecular weight PLGA copolymer is 40,000-80,000 Da in the molecular weight, and the mass ratio of the high-molecular weight PLGA copolymer to the low-molecular weight PLGA copolymer is between 25:75 and 3:97.

In a class of this embodiment, a total mass of the second fiber accounts for 1%-25% of a total mass of the first fiber, such as 1%, 5%, 8%, 10%, 15%, 18%. %, 20%, or 25%, preferably 1%-15%.

A drug release curve is affected by the content of the second fiber in the drug-loaded nanofiber membrane. Increased content of the second fiber leads to fast release of the drug, thereby controlling the drug release cycle. The total mass of the second fiber is accounted for 1%-25% of the total mass of the first fiber to control the drug release cycle within a range from 1 day to 26 days.

In a class of this embodiment, a molar ratio of lactic acid unit to hydroxyacetic acid unit in the PLGA copolymer is between 1:1 and 9:1, such as, 1:1, 2:1, 3:1, 3.5:1, 4:1, 5:1, 5.5:1, 6:1, 7:1, 8:1, or 9:1.

In a class of this embodiment, a molecular weight of PDO is 60000-250,000 Da, such as 60000 Da, 80000 Da, 100,000 Da, 120,000 Da, 150,000 Da, 180,000 Da, 200,000 Da, or 250,000 Da.

In a class of this embodiment, the drug comprises an antibiotic drug, an anti-tumor drug, an anti-inflammatory drug, or a combination thereof.

In a class of this embodiment, the drug comprises ciprofloxacin, ciprofloxacin hydrochloride, moxifloxacin, levofloxacin, cefradine, tinidazole, 5-fluorouracil, adriamycin, cisplatin, paclitaxel, gemcitabine, capecitabine, aspirin, indomethacin, or a combination thereof.

The drug of the disclosure includes, but is not limited to, the drug described above and a pharmaceutically acceptable drug thereof.

In a class of this embodiment, a total mass of the drug accounts for 1%-35% of a total mass of the first fiber and the second fiber, such as 1%, 2%, 5%, 8%, 10%, 15%, 20%, 25%, 30%, or 35%.

When the total mass of the drug exceeds 35% of the total mass of the two fibers, the drug is suddenly released, causing toxicity due to a high local concentration of the drug; when the total mass of the drug is less than 1% of the total mass of the two fibers, an effective onset concentration cannot be reached.

Another objective of the disclosure is to provide a method for preparing the drug-loaded nanofiber membrane, the method comprising:

1) mixing the drug and the PLGA copolymer in a first solvent to yield a first mixed solution; and mixing PDO in a second solvent to yield a second mixed solution; and
2) separately taking a part of the first mixed solution and the second mixed solutions in 1), and introducing the part of the first and the second mixed solutions to a multi-nozzle electrostatic spinning apparatus for electrostatic spinning, thereby obtaining a drug-loaded nanofiber membrane.

The drug-loaded nanofiber membrane of the disclosure is stable in nature and has high porosity, similar to an extracellular matrix, and is applied to a postoperative stump without the need for secondary surgery, and is degradable in the body.

When the multi-nozzle electrostatic spinning apparatus is used for electrostatic spinning, a plurality of first and the second mixed solutions is loaded with a spot-spaced method, and the first mixed solution is loaded in more syringes. For example, with seven nozzles, the first nozzle, the second nozzle, the third nozzle, the fifth nozzle, the sixth nozzle and the seventh nozzle are loaded with a mixed solution of the drug, the PLGA copolymer, and the solvent. The fourth nozzle is loaded with a mixed solution of PDO and the solvent. Alternatively, the first nozzle, the third nozzle, the fifth nozzle and the seventh nozzle are loaded with a mixed solution of the drug, the PLGA copolymer, and the solvent, and the second nozzle, the fourth nozzle and the sixth nozzle are loaded with PDO and the solvent. In this way, the two fibers in a system can be mixed more evenly.

In a class of this embodiment, in 1), the solvent is selected from the group consisting of N, N-dimethylformamide, acetone, hexafluoroisopropanol, or a combination thereof.

In a class of this embodiment, in 1), the drug and the PLGA copolymer are stirred in the first solvent at 40-50° C. for mixing (for example, 40° C., 42° C., 44° C., 45° C., 46° C., 48° C., or 50° C.).

In a class of this embodiment, an inner diameter of a nozzle for electrostatic spinning is 0.4 mm during electrostatic spinning.

In a class of this embodiment, a voltage for the electrostatic spinning is 10-25 kV, such as 10 kV, 12 kV, 13 kV, 14 kV, 15 kV, 16 kV, 18 kV, 20 kV, 22 kV, 24 kV, or 25 kV, preferably 20-25 kV.

In a class of this embodiment, a spinning distance for the electrostatic spinning is 5-15 cm, such as 5 cm, 6 cm, 7 cm, 8 cm, 9 cm, 10 cm, 12 cm, 14 cm, or 15 cm, preferably 8-15 cm.

In a class of this embodiment, a temperature for the electrostatic spinning is 20-30° C., such as 20° C., 21° C., 22° C., 23° C., 24° C., 25° C., 26° C., 27° C., 28° C., 29° C., or 30° C.

In a class of this embodiment, an advancing speed of each mixed solution for the electrostatic spinning is 4-10 mL/L, for example, 4 mL/L, 5 mL/L, 6 mL/L, 7 mL/L, 8 mL/L, 9 mL/L, or 10 mL/L, preferably 6-10 mL/L.

In a class of this embodiment, a receiving device during the electrostatic spinning is a metal drum with a diameter of 5-15 cm (for example, 5 cm, 6 cm, 8 cm, 10 cm, 12 cm, 14 cm, or 15 cm), and a rotation speed is 600-900 rpm (such as 600 rpm, 650 rpm, 700 rpm, 750 rpm, 800 rpm, 850 rpm, or 900 rpm), preferably 800 rpm.

In a class of this embodiment, in 2), the drug-loaded nanofiber membrane is post-processed as follows: the drug-loaded nanofiber membrane is vacuum-dried at 20-30° C. (for example, 20° C., 21° C., 22° C., 23° C., 24° C., 25° C., 26° C., 27° C., 28° C., 29° C., or 30° C.) for 24-72 h (for example, 24 h, 30 h, 35 h, 50 h, 60 h, or 72 h).

Preferably, a method for preparing the drug-loaded nanofiber membrane comprises:

1) mixing the drug and the PLGA copolymer in a first solvent to yield a first mixed solution; and mixing PDO in a second solvent to yield a second mixed solution;
2) respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 20-30° C. to obtain a drug-loaded nanofiber membrane, where the nozzle of the multi-nozzle electrostatic spinning apparatus has an inner diameter of 0.4 mm; an advancing speed of each mixed solution is 4-10 mL/L, a spinning voltage is 10-25 kV, a spinning distance is 5-15 cm, a receiving device is a metal drum with a diameter of 5-15 cm; a rotation speed of the metal drum is 600-900 rpm; and
3) vacuum-drying the drug-loaded nanofiber membrane in 2) at 20-30° C. for 24-72 h.

In another aspect, the disclosure provides a method for preparing a drug delivery system, the method comprising applying the drug-loaded nanofiber membrane.

The following advantages are associated with the drug-loaded nanofiber membrane of the disclosure:

1. The PLGA copolymer and PDO are extruded separately to form a first fiber and a second fiber, and the drug is dispersed into the first fiber; the first fiber has a relatively high swelling capacity, which allows the first fiber to swell in vivo and bond together, thereby blocking drug release from the channels in the first fiber; the second fiber has a relatively low swelling capacity, and the fibers are difficult to bond together, thereby supporting the poly(lactic-co-glycolic acid) copolymer to form a part of channels for the release of the drug; and
2. The drug-loaded nanofiber membrane of the disclosure is stable in nature and has high porosity, similar to an extracellular matrix, and is applied to a postoperative stump without the need for secondary surgery, and is degradable in the body.

DETAILED DESCRIPTION

To further illustrate, embodiments detailing a drug-loaded nanofiber membrane, a method for preparing the same, and application thereof are described below. It should be noted that the following embodiments are intended to describe and not to limit the disclosure.

Example 1

A drug-loaded nanofiber membrane comprises a first fiber, a second fiber, and paclitaxel; a PLGA copolymer and PDO are extruded separately to form the first fiber and the second fiber; paclitaxel is dispersed into the first fiber; a mass ratio of a high-molecular weight PLGA copolymer (MW=150000) to a low-molecular weight PLGA copolymer (MW=80000) is 25:75; a total mass of the second fiber accounts for 10% of a total mass of the first fiber; and a total mass of paclitaxel accounts for 10% of a total mass of the two fibers.

A method for preparing the drug-loaded nanofiber membrane comprises:
1. mixing paclitaxel, the PLGA copolymer in acetone to obtain a first mixed solution; and mixing PDO in hexafluoroisopropanol to obtain a second mixed solution; and
2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 5 mL/L, the spinning voltage is 15 kV, the spinning distance is 5 cm, the receiving device is the metal drum with the diameter of 5 cm; the rotation speed of the metal drum is 600 rpm; and
3. vacuum-drying the drug-loaded nanofiber membrane in 2) at 25° C. for 24 h.

Figure 1:
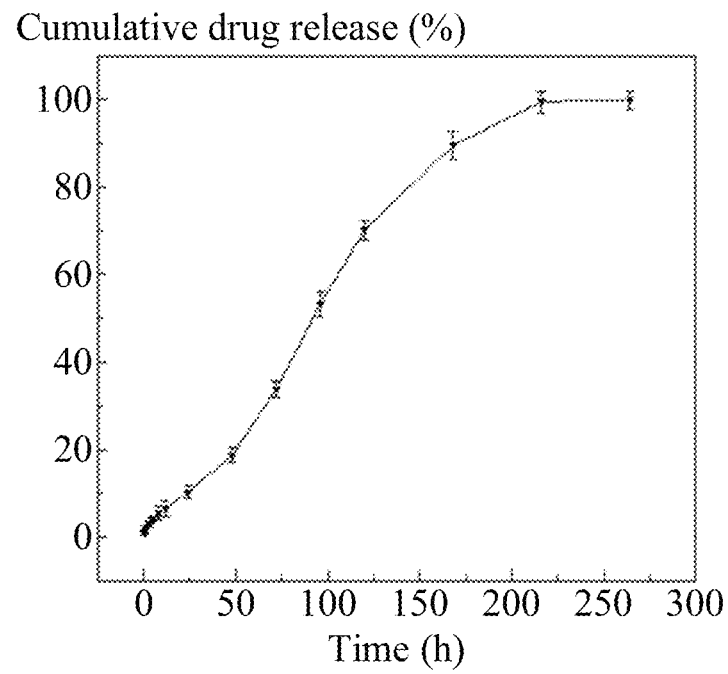
FIG. 1 is a drug release curve of a drug-loaded nanofiber membrane prepared in Example 1.

The drug-loaded nanofiber membrane was tested for drug release, and the drug release curve was drawn as follows: the dried drug-loaded nanofiber membrane was cut into 10 mg samples, put into a centrifuge tube with 10 mL of a fresh phosphate buffered saline (PBS) solution, and then put in an air bath constant temperature shaker at a temperature of 37° C. and a shaking speed of 100 rpm. At designated time intervals, 1 mL of release solution was taken out, and an equal amount of the fresh PBS solution was added. Then, a standard curve of the drug' concentration was measured with an ultraviolet-visible spectrophotometer, and the amount of drug released by the drug-loaded nanofiber membrane was determined according to the standard curve. All experimental groups were in five copies, and the measured drug release amount was expressed as mean±standard deviation. The experimental results were shown in FIG. 1. The drug release system presented a release cycle of nearly 11 days. At 24 h, the drug release rate was greatly accelerated until the drug was completely released.

Figure 7:
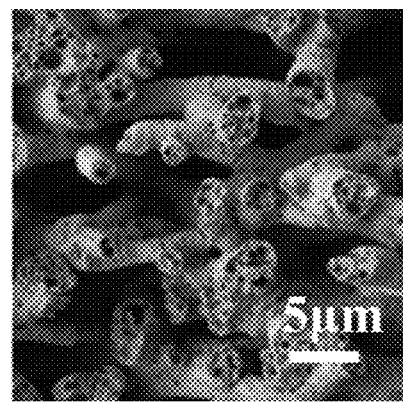
FIG. 7 is a scanning electron micrograph showing a cross-sectional view of a drug-loaded nanofiber membrane prepared in Example 1.

The drug-loaded nanofiber membrane was scanned with an electron microscope. Specifically, the drug-loaded nanofiber membrane was soaked in PBS for 7 days, rinsed with deionized water several times, and dried in a vacuum-drying oven for 48 h. Prior to observation of cross-sectional morphology, the dried sample was immersed into liquid nitrogen, broken, attached to a sample stage, and coated with a layer of platinum by a vacuum sputtering system. The experimental results were shown in FIG. 7. When the drug-loaded nanofiber membrane was soaked in PBS for 7 days, the drug-loaded nanofiber membrane continued to swell, which decreased the gap between the fibers, causing a small part of the fibers to bond together.

Example 2

A drug-loaded nanofiber membrane comprises a first fiber, a second fiber, and fluorouracil; a PLGA copolymer and PDO are extruded separately to form the first fiber and the second fiber; fluorouracil is dispersed into the first fiber; a mass ratio of a high-molecular weight PLGA copolymer (MW=100000) to a low-molecular weight PLGA copolymer (MW=40000) is 15:85; a total mass of the second fiber accounts for 15% of a total mass of the first fiber; and a total mass of fluorouracil accounts for 20% of a total mass of the two fibers.

A method for preparing the drug-loaded nanofiber membrane comprises:
1. mixing fluorouracil, the PLGA copolymer in acetone to obtain a first mixed solution; and mixing PDO in hexafluoroisopropanol to obtain a second mixed solution; and
2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 10 mL/L, the spinning voltage is 25 kV, the spinning distance is 10 cm, the receiving device is the metal drum with the diameter of 5 cm; the rotation speed of the metal drum is 800 rpm; and
3. vacuum-drying the drug-loaded nanofiber membrane in 2) at 25° C. for 48 h.

Figure 2:
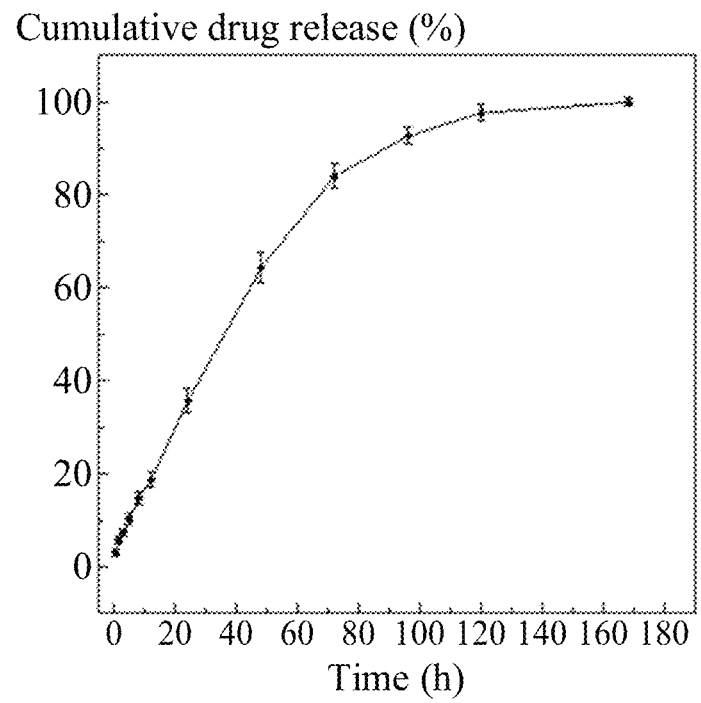
FIG. 2 is a drug release curve of a drug-loaded nanofiber membrane prepared in Example 2.

The drug-loaded nanofiber membrane was tested for drug release, and the drug release curve was drawn following the method of Example 1. The experimental results were shown in FIG. 2. The drug release system presented a release cycle of nearly 7 days, without a sudden release of the drug. At 18 h, the drug release rate was greatly accelerated and most of the drug had been released on the $5^{th}$ day.

Figure 8:
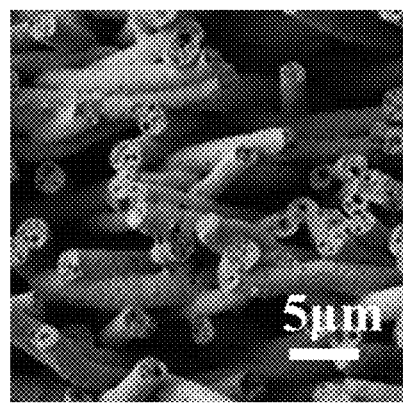
FIG. 8 is a scanning electron micrograph showing a cross-sectional view of a drug-loaded nanofiber membrane prepared in Example 2.

Following the method of Example 1, the drug-loaded nanofiber membrane was scanned with an electron microscope. The experimental results were shown in FIG. 8. When the drug-loaded nanofiber membrane was soaked in PBS for 7 days, the drug-loaded nanofiber membrane continued to swell, causing a part of the fibers to bond together.

Example 3

A drug-loaded nanofiber membrane comprises a first fiber, a second fiber, and capecitabine; a PLGA copolymer and PDO are extruded separately to form the first fiber and the second fiber; capecitabine is dispersed into the first fiber; a mass ratio of a high-molecular weight PLGA copolymer (MW=120000) to a low-molecular weight PLGA copolymer (MW=60000) is 5:95; a total mass of the second fiber accounts for 1% of a total mass of the first fiber; and a total mass of capecitabine accounts for 15% of a total mass of the two fibers.

A method for preparing the drug-loaded nanofiber membrane comprises:
1. mixing capecitabine, the PLGA copolymer in acetone to obtain a first mixed solution; and mixing PDO in hexafluoroisopropanol to obtain a second mixed solution; and
2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 8 mL/L, the spinning voltage is 10 kV, the spinning distance is 15 cm, the receiving device is the metal drum with the diameter of 5 cm; the rotation speed of the metal drum is 900 rpm; and
3. vacuum-drying the drug-loaded nanofiber membrane in 2) at 25° C. for 72 h.

Figure 3:
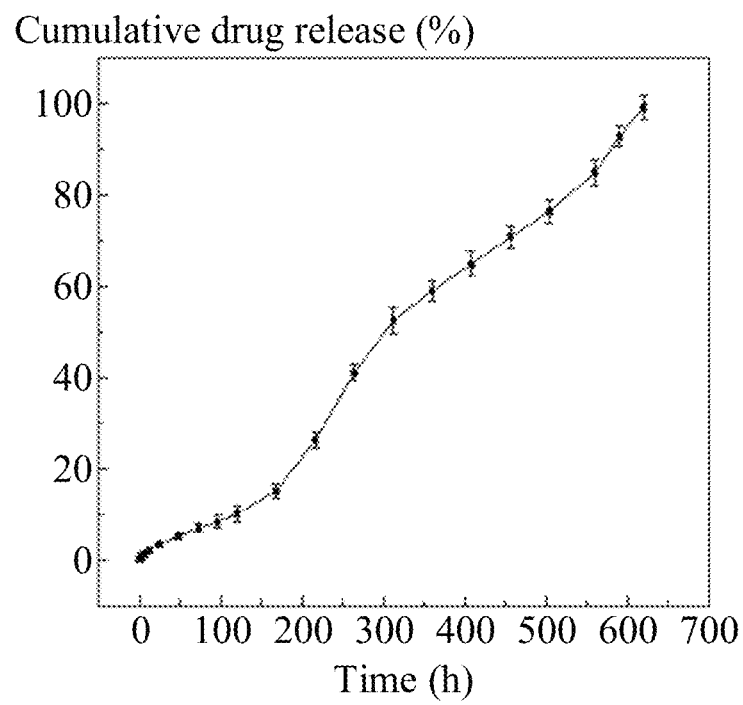
FIG. 3 is a drug release curve of a drug-loaded nanofiber membrane prepared in Example 3.

The drug-loaded nanofiber membrane was tested for drug release, and the drug release curve was drawn following the method of Example 1. The experimental results were shown in FIG. 3. The drug release system presented a release cycle of nearly 26 days, without a sudden release of the drug. The drug release curve was similar to that of a fibrous membrane only comprising PLGA. On the $7^{th}$ day, the drug release rate was greatly accelerated until the drug was completely released.

Figure 9:
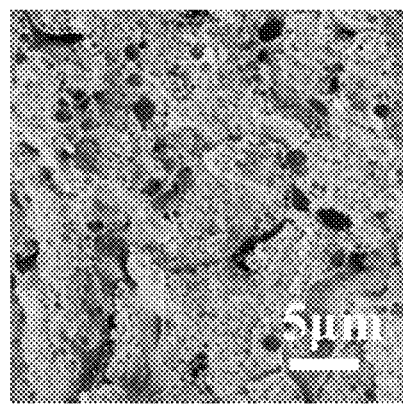
FIG. 9 is a scanning electron micrograph showing a cross-sectional view of a drug-loaded nanofiber membrane prepared in Example 3.

Following the method of Example 1, the drug-loaded nanofiber membrane was scanned with an electron microscope. The experimental results were shown in FIG. 9. When the drug-loaded nanofiber membrane was soaked in PBS for 7 days, the drug-loaded nanofiber membrane continued to swell, which further decreased the gap between the fibers, causing most of the fibers to bond together.

Example 4

A drug-loaded nanofiber membrane comprises a first fiber, a second fiber, and ciprofloxacin; a PLGA copolymer and PDO are extruded separately to form the first fiber and the second fiber; ciprofloxacin is dispersed into the first fiber; a mass ratio of a high-molecular weight PLGA copolymer (MW=150000) to a low-molecular weight PLGA copolymer (MW=60000) is 3:97; a total mass of the second fiber accounts for 5% of a total mass of the first fiber; and a total mass of ciprofloxacin accounts for 10% of a total mass of the two fibers.

A method for preparing the drug-loaded nanofiber membrane comprises:
1. mixing ciprofloxacin, the PLGA copolymer in acetone to obtain a first mixed solution; and mixing PDO in hexafluoroisopropanol to obtain a second mixed solution; and
2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 6 mL/L, the spinning voltage is 15 kV, the spinning distance is 15 cm, the receiving device is a metal drum with the diameter of 5 cm; the rotation speed of the metal drum is 600 rpm; and
3. vacuum-drying the drug-loaded nanofiber membrane in 2) at 25° C. for 72 h.

Figure 4:
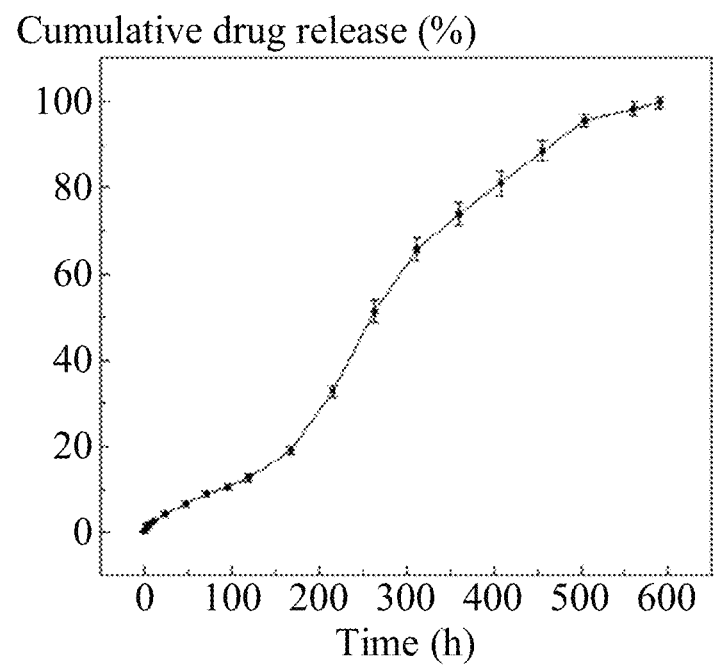
FIG. 4 is a drug release curve of a drug-loaded nanofiber membrane prepared in Example 4.

The drug-loaded nanofiber membrane was tested for drug release, and the drug release curve was drawn following the method of Example 1. The experimental results were shown in FIG. 4. The drug release system presented a release cycle of nearly 25 days, without a sudden release of the drug. On the $5^{th}$ day, the drug release rate was greatly accelerated until the drug was completely released.

Figure 10:
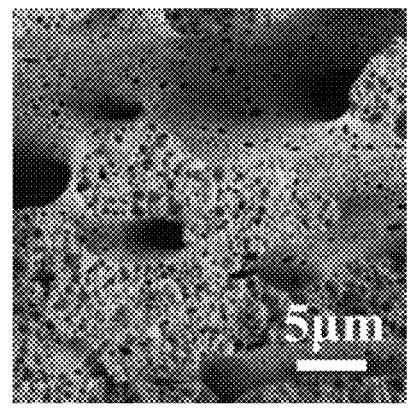
FIG. 10 is a scanning electron micrograph showing a cross-sectional view of a drug-loaded nanofiber membrane prepared in Example 4.

Following the method of Example 1, the drug-loaded nanofiber membrane was scanned with an electron microscope. The experimental results were shown in FIG. 10. When the drug-loaded nanofiber membrane was soaked in PBS for 7 days, the drug-loaded nanofiber membrane continued to swell, which further decreased the gap between the fibers, causing most of the fibers to bond together.

Example 5

A drug-loaded nanofiber membrane comprises a first fiber, a second fiber, and cefradine; a PLGA copolymer and PDO are extruded separately to form the first fiber and the second fiber; cefradine is dispersed into the first fiber; a mass ratio of a high-molecular weight PLGA copolymer (MW=150000) to a low-molecular weight PLGA copolymer (MW=60000) is 10:90; a total mass of the second fiber accounts for 7% of a total mass of the first fiber; and a total mass of cefradine accounts for 10% of a total mass of the two fibers.

A method for preparing the drug-loaded nanofiber membrane comprises:
1. mixing cefradine, the PLGA copolymer in acetone to obtain a first mixed solution; and mixing PDO in hexafluoroisopropanol to obtain a second mixed solution; and
2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 6 mL/L, the spinning voltage is 15 kV, the spinning distance is 15 cm, the receiving device is the metal drum with the diameter of 5 cm; the rotation speed of the metal drum is 600 rpm; and 3. vacuum-drying the drug-loaded nanofiber membrane in 2) at 25° C. for 24 h.

Figure 5:
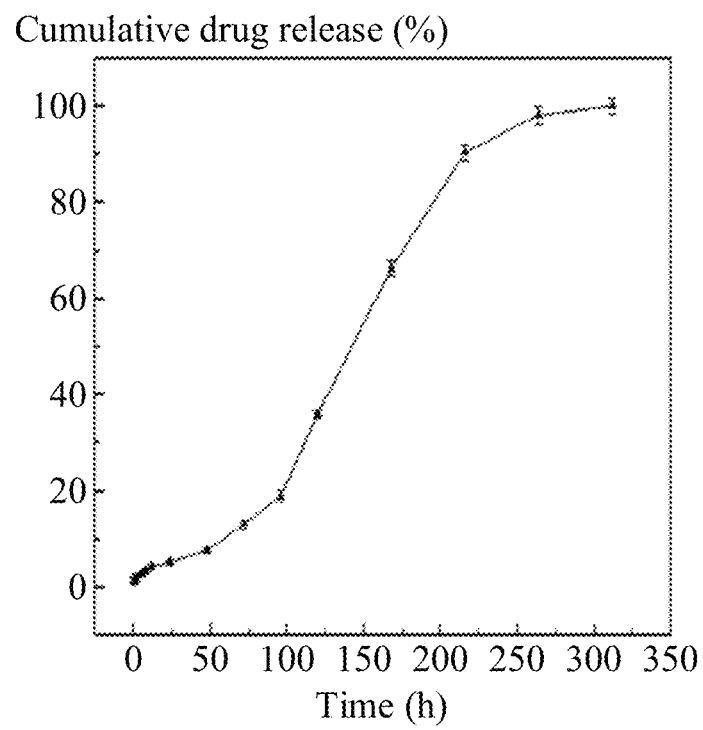
FIG. 5 is a drug release curve of a drug-loaded nanofiber membrane prepared in Example 5.

The drug-loaded nanofiber membrane was tested for drug release, and the drug release curve was drawn following the method of Example 1. The experimental results were shown in FIG. 5. The drug release system presented a release cycle of nearly 15 days, without a sudden release of the drug. On the 4$^{th}$ day, the drug release rate was greatly accelerated until the drug was completely released.

Figure 11:
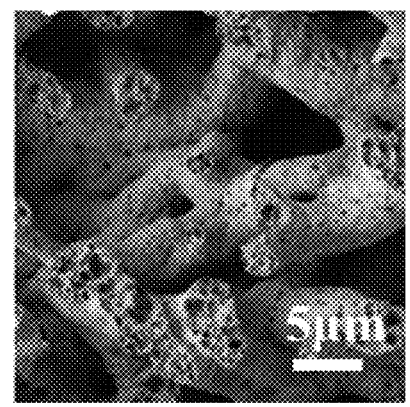
FIG. 11 is a scanning electron micrograph showing a cross-sectional view of a drug-loaded nanofiber membrane prepared in Example 5.

Following the method of Example 1, the drug-loaded nanofiber membrane was scanned with an electron microscope. The experimental results were shown in FIG. 11. When the drug-loaded nanofiber membrane was soaked in PBS for 7 days, the drug-loaded nanofiber membrane continued to swell, which further decreased the gap between the fibers, causing a part of the fibers to bond together.

Example 6

A drug-loaded nanofiber membrane comprises a first fiber, a second fiber, and levofloxacin; a PLGA copolymer and PDO are extruded separately to form the first fiber and the second fiber; levofloxacin is dispersed into the first fiber; a mass ratio of a high-molecular weight PLGA copolymer (MW=150000) to a low-molecular weight PLGA copolymer (MW=60000) is 10:90; a total mass of the second fiber accounts for 25% of a total mass of the first fiber; and a total mass of levofloxacin accounts for 10% of a total mass of the two fibers.

A method for preparing the drug-loaded nanofiber membrane comprises:

1. mixing levofloxacin, the PLGA copolymer in acetone to obtain a first mixed solution; and mixing PDO in hexafluoroisopropanol to obtain a second mixed solution; and 2. respectively loading the first mixed solution and the second mixed solution in 1) into a 22G flat-head dispensing syringe, introducing the first mixed solution and the second mixed solution to a multi-nozzle electrostatic spinning apparatus for electrostatic spinning at 25° C. to obtain a drug-loaded nanofiber membrane, where the nozzle of the multi-nozzle electrostatic spinning apparatus has an inner diameter of 0.4 mm; the advancing speed of each mixed solution is 6 mL/L, the spinning voltage is 15 kV, the spinning distance is 15 cm, the receiving device is the metal drum with the diameter of 5 cm; the rotation speed of the metal drum is 600 rpm; and 3. vacuum-drying the drug-loaded nanofiber membrane in 2) at 25° C. for 24 h.

Figure 6:
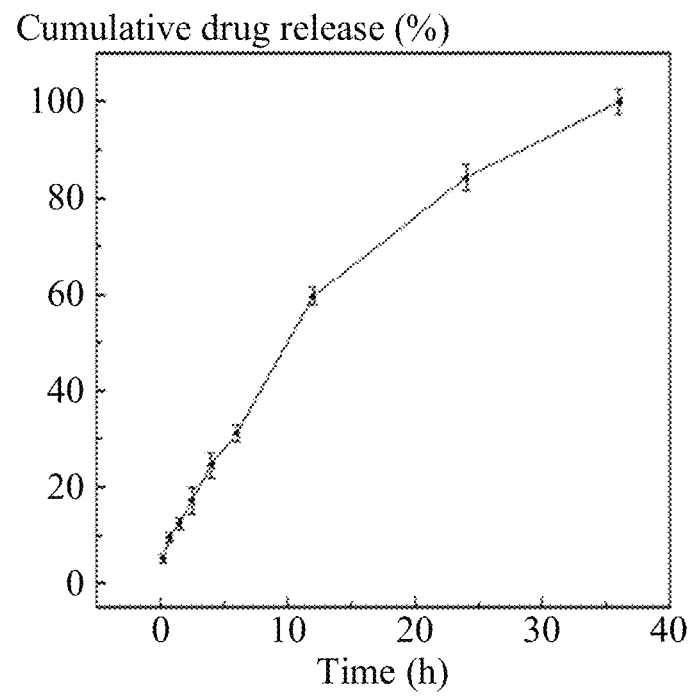
FIG. 6 is a drug release curve of a drug-loaded nanofiber membrane prepared in Example 6.

The drug-loaded nanofiber membrane was tested for drug release, and the drug release curve was drawn following the method of Example 1. The experimental results were shown in FIG. 6. The drug release system presented a release cycle of nearly 1 days, without a sudden release of the drug.

Figure 12:
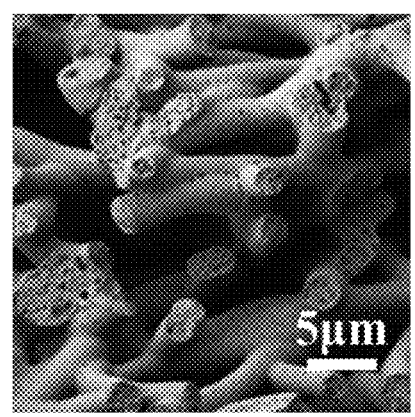
FIG. 12 is a scanning electron micrograph showing a cross-sectional view of a drug-loaded nanofiber membrane prepared in Example 6.

Following the method of Example 1, the drug-loaded nanofiber membrane was scanned with an electron microscope. The experimental results were shown in FIG. 12. When the drug-loaded nanofiber membrane was soaked in PBS for 7 days, an increased gap between the fibers of the drug-loaded nanofiber membrane causes only a few fibers to bond together.

It will be obvious to those skilled in the art that changes and modifications may be made, and therefore, the aim in the appended claims is to cover all such changes and modifications.

The invention claimed is:

1. A drug-loaded nanofiber membrane comprising a first fiber and a second fiber; the first fiber comprises poly(lactic-co-glycolic acid) copolymer (PLGA copolymer) and a drug dispersed within the first fiber, and the second fiber comprises poly(p-dioxanone) (PDO);

wherein:
the PLGA copolymer is a mixture consisting of a high-molecular weight PLGA copolymer and a low-molecular weight PLGA copolymer; the high-molecular weight refers to a viscosity-average molecular weight of 100,000 to 150,000 Da, and the low-molecular weight refers to a viscosity-average molecular weight of 40,000 to 80,000 Da;
a mass ratio of the high-molecular weight PLGA copolymer to the low-molecular weight PLGA copolymer is between 25:75 and 3:97; and
a total mass of the second fiber accounts for 1%-25% of a total mass of the first fiber.

2. The membrane of claim 1, wherein the total mass of the second fiber accounts for 1%-15% of a total mass of the first fiber.

3. The membrane of claim 1, wherein a molar ratio of lactic acid unit to hydroxyacetic acid unit in the PLGA copolymer is between 1:1 and 9:1.

4. The membrane of claim 1, wherein a molecular weight of PDO is 60000-250,000 Da.

5. The membrane of claim 1, wherein the drug comprises an antibiotic drug, an anti-tumor drug, an anti-inflammatory drug, or a combination thereof.

6. The membrane of claim 5, wherein the drug comprises ciprofloxacin, ciprofloxacin hydrochloride, moxifloxacin, levofloxacin, cefradine, tinidazole, 5-fluorouracil, adriamycin, cisplatin, paclitaxel, gemcitabine, capecitabine, aspirin, indomethacin, or a combination thereof.

7. The membrane of claim 1, wherein a total mass of the drug accounts for 1%-35% of a total mass of the first fiber and the second fiber.

8. A drug-loaded nanofiber membrane comprising a first fiber, a second fiber, and a drug dispersed into the first fiber; the first fiber comprising poly(lactic-co-glycolic acid) copolymer (PLGA copolymer), and the second fiber comprising poly(p-dioxanone) (PDO);

wherein:
the PLGA copolymer is a mixture of a high-molecular weight PLGA copolymer and a low-molecular weight PLGA copolymer; the high-molecular weight refers to a viscosity-average molecular weight of 100,000 to 150,000 Da, and the low-molecular weight refers to a viscosity-average molecular weight of 60,000 to 80,000 Da;
a mass ratio of the high-molecular weight PLGA copolymer to the low-molecular weight PLGA copolymer is between 25:75 and 3:97; and
a total mass of the second fiber accounts for 1%-25% of a total mass of the first fiber.

9. The membrane of claim 8, wherein the low-molecular weight refers to a viscosity-average molecular weight of 70,000 to 80,000 Da.

* * * * *

UNITED STATES PATENT AND TRADEMARK OFFICE
CERTIFICATE OF CORRECTION

PATENT NO. : 12,178,796 B2  
APPLICATION NO. : 17/467427  
DATED : December 31, 2024  
INVENTOR(S) : Zhichao Han et al.

Page 1 of 1

It is certified that error appears in the above-identified patent and that said Letters Patent is hereby corrected as shown below:

On the Title Page

Please amend item (72) to include the following inventor, in addition to those already listed:
— Hao CHEN, Shenzhen (CN) —

Signed and Sealed this  
Eighth Day of July, 2025

Coke Morgan Stewart  
*Acting Director of the United States Patent and Trademark Office*